(12) United States Patent
McCulloch et al.

(10) Patent No.: US 11,850,168 B2
(45) Date of Patent: Dec. 26, 2023

(54) TENSOR FASCIA LATAE (TFL) PROTECTOR

(71) Applicant: Invictus Orthopaedics LLC, Teaneck, NJ (US)

(72) Inventors: Kenneth McCulloch, Manhasset, NY (US); Anthony D'Antuono, South Amboy, NJ (US); Troy Lane, Murrells Inlet, SC (US)

(73) Assignee: Invictus Orthopaedics LLC, Teaneck, NJ (US)

( * ) Notice: Subject to any disclaimer, the term of this patent is extended or adjusted under 35 U.S.C. 154(b) by 198 days.

(21) Appl. No.: 17/671,499

(22) Filed: Feb. 14, 2022

(65) Prior Publication Data

US 2022/0331125 A1 Oct. 20, 2022

Related U.S. Application Data

(62) Division of application No. 15/899,671, filed on Feb. 20, 2018, now Pat. No. 11,273,055.

(60) Provisional application No. 62/461,280, filed on Feb. 21, 2017.

(51) Int. Cl.
| | | |
|---|---|---|
| *A61F 2/46* | (2006.01) | |
| *A61F 2/30* | (2006.01) | |
| *A61B 17/02* | (2006.01) | |
| *A61B 17/56* | (2006.01) | |

(52) U.S. Cl.
CPC .......... *A61F 2/4609* (2013.01); *A61B 17/02* (2013.01); *A61F 2/30721* (2013.01); *A61B 17/56* (2013.01)

(58) Field of Classification Search
CPC ............... A61F 2/4609; A61F 2017/0275
See application file for complete search history.

(56) References Cited

U.S. PATENT DOCUMENTS

| | | |
|---|---|---|
| 2009/0012370 A1 | 1/2009 | Gutierrez et al. |
| 2013/0197313 A1 | 8/2013 | Wan |
| 2015/0119648 A1 | 4/2015 | Barnett |
| 2016/0228115 A1 | 8/2016 | Swift |

FOREIGN PATENT DOCUMENTS

EP 2 873 376 A1 2/2019

OTHER PUBLICATIONS

Office Action dated May 4, 2020 in U.S. Appl. No. 15/899,671.
Office Action dated Sep. 23, 2023 in U.S. Appl. No. 15/899,671.
International Preliminary Report on Patentability dated Aug. 27, 2019 in International Application No. PCT/US18/18723 (7 sheets).
Notification of Transmittal of the International Search Report and the Written Opinion of the International Searching Authority, or the Declaration dated Jun. 14, 2018 in International Application No. PCT/US18/18723 (12 sheets).

*Primary Examiner* — Olivia C Chang
(74) *Attorney, Agent, or Firm* — Collard & Roe, P.C.

(57) ABSTRACT

A TFL Protector for use during a total hip arthroplasty having a generally semi-circular or U-shaped elongate body includes a distal end, a proximal end, an elbow and a convex surface opposite a concave surface. The generally U-shaped or semi-circular elongated body extends from the distal end to the proximal end and the proximal end turns back toward back toward the distal end at elbow.

5 Claims, 4 Drawing Sheets

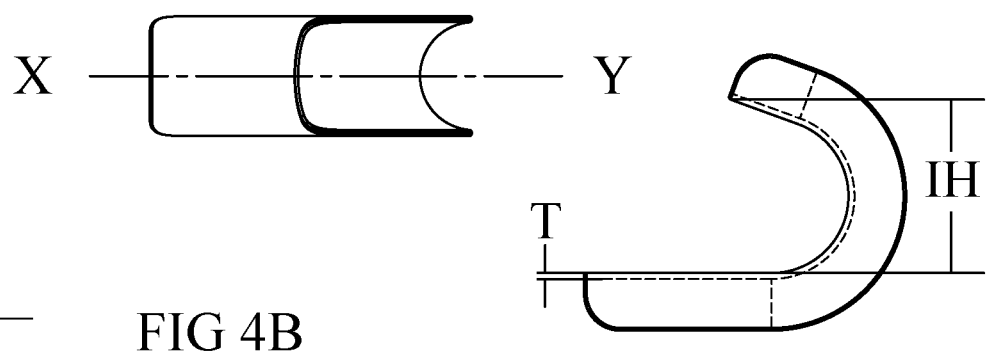
FIG 4A
FIG 4D
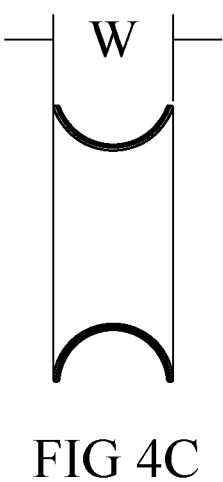
FIG 4B
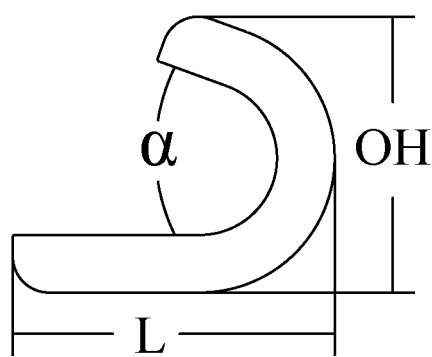
FIG 4C
FIG 4E

TENSOR FASCIA LATAE (TFL) PROTECTOR

CROSS REFERENCE TO RELATED APPLICATIONS

The present application is a divisional of pending U.S. patent application Ser. No. 15/899,671 filed on Feb. 20, 2018, which claims the benefit of U.S. Provisional Application No. 62/461,280, filed on Feb. 21, 2017, both of which are incorporated herein by reference in their entireties.

FIELD OF THE INVENTION

The present invention generally relates to the field of orthopedic surgery, and more particularly, the present invention is relates a tensor fascia latae (TFL) protector.

BACKGROUND OF THE INVENTION

The hip is one of the body's largest joints. It is a ball-and-socket joint. The socket is formed by the acetabulum, which is part of the large pelvis bone. The ball is the femoral head, which is the upper end of the femur (thigh bone). The bone surfaces of the ball and socket are covered with articular cartilage, a smooth tissue that cushions the ends of the bones and enables them to move easily. A thin tissue called synovial membrane surrounds the hip joint. In a healthy hip, this membrane makes a small amount of fluid that lubricates the cartilage and eliminates almost all friction during hip movement.

When the hip joint becomes damaged or diseased, the patient can experience pain and discomfort, often to debilitating levels greatly reducing mobility and quality of life. Common causes of hip damage include: osteoarthritis; rheumatoid arthritis; post-tramatic arthritis; avascular necrosis; childhood hip disease; traumatic injury, and deformity. All can lead to damage to bone or cartilage associated with the femoral head or the acetabulum, or both.

FIG. 1 illustrates the basic anatomy of the human hip including the bones of the hip, namely the acetabulum, the femoral head, the neck of the femur, the lesser trochanter, and the femur. FIG. 2 illustrates muscles and soft tissue around the hip, including the sartorius, tensor fascia latae, gluteous medius, anterior superior iliac spine, and the rectus femoris.

In severe or chronic cases, total hip replacement (also called total hip arthroplasty ("THA")) can greatly improve the quality of life for the patient. In total hip replacement surgery the damaged bone and cartilage is removed and replaced with prosthetic components. The damaged femoral head is removed and replaced with a metal stem that is placed into the hollow center of the femur. The femoral stem may be either cemented or press fit into the bone. A metal or ceramic ball is placed on the upper part of the stem. This ball replaces the damaged femoral head that was removed. The damaged cartilage surface of the socket (acetabulum) is removed and replaced with a metal socket. Screws or cement are sometimes used to hold the socket in place. A polyethelene, ceramic, or metal spacer is inserted between the new ball and the socket to allow for a smooth gliding surface.

In order to place the implant a surgeon must gain access to and expose the hip joint, and particularly the femoral head and the acetabulum. There are several procedures for accessing the hip joint through the soft tissue of the patient. These procedures include various approaches, including the direct anterior approach, anterolateral approach, lateral approach, posterior approach, medial approach, and lateral subtrochanteric and proximal femoral shaft approaches. Approaches to the hip are described in the Atlaos of Orthopaeid Surgery, Vol. 3, Lower Extremity; Laurin, C A et al., Editors, copyright 1991, incorporated herein by reference in its entirety.

Surgical approaches and exposures produce some degree of tissue damage. The anterior approach utilizes the interval between Sartorius and tensor fascia latae and can, in many instances cause collateral tissue damage and increase patient recovery times. In the direct lateral approach, the tensor fascia latae (TFL) is retracted to expose the gluteus maximus. In the anterolateral approach, the TFL is retracted anteriorly and the gluteus medius is retracted posteriorly to expose the joint capsule. In the anterior approach both the access to the hip can often be achieves without any muscular releases or detachments.

The anterior iliofemoral approach utilizes the interval between the Sartorius muscle and the tensor fascia lata muscle. The entire ilium and hip joint can be reached through the iliac part of the incision. Nearly all hip surgery can be carried out through this approach and separate parts can be used for different purposes. However, it is now mainly used to expose the anterolateral aspect of the head and neck of the femur and acetabulum for biopsy or excision of bone in this area. It is difficult to gain direct access to the entire acetabulum, or to deliver the proximal femur out of the wound without extensive stripping of the abductors from the ilium or transecting the external rotator tendons. The lower or distal part of the approach, requires no stripping of muscles, except possibly release of the tendinous origin of the rectus femoris.

With the patient supine a pad is placed under the affected hip so that the posterior aspect of the ilium can be exposed, when necessary, and also to facilitate anterior dislocation of the hip. The leg is draped so the hip and leg can be manipulated during the approach. The skin incision begins at the middle of the iliac crest, 2 centimeters below the crest of the ilium to avoid a painful postoperative scar adherent to bone. The incision is extended anteriorly below the anterior superior iliac spine and curved distally on the lateral aspect of the thigh. The superficial and deep fascia over the Sartorius muscle are divided, medial to the tensor fascia lata muscle. The lateral femoral cutaneous nerve that penetrates the deep fascia just below the anterior superior iliac spine is identified and retracted medially along with the Sartorius muscle. The interval between the tensor fascia lata and the Sartorius is more easily identified distal to the anterior superior iliac spine; so the dissection should therefore be started distally rather than close to the anterior superior iliac spine. Part of the anterior aspect of the origin of the tensor fascia is subperiosteally stripped from the ilium. Retraction in this interval exposes the gluteus medius muscle and the rectus femoris muscle, which at this level is easily identified because of its fibrous nature, in contrast to the fleshy surrounding muscles.

The ascending branches of the lateral femoral cutaneous circumflex vessels are usually ligated at the lower end of the incision. The tendinous origin of the rectus femoris is separated from the underlying joint capsule, and the direct and reflected origins are released by a transverse cut. The iliopsoas is also separated from the capsule by blunt dissection and retracted medially. Most of the anterior aspect of the hip joint is then exposed. The capsule may be incised in line with the axis of the femoral neck and transversely at the edge of the acetabulum, as well as distally (in the form of the letter H). If it is necessary to dislocate the hip anteriorly, as much of the capsule is incised or excised as necessary; part of the labrum may also be excised. The femoral head is dislocated by adducting, externally rotating and extending the hip. In young patients, it may be necessary to incise the ligamentum teres before the hip can be completely dislocated. The release of the psoas tendon from the lesser trochanter may also be required. The lesser trochanter is exposed by externally rotating the leg, retracting the psoas medially away from the capsule. To expose more of the ilium or the superior aspect of the acetabulum, the abductor muscle origin is stripped subperiosteally from the wing of the ilium and retracted posteriorly and laterally.

Using the anterior approach (or other approaches) the surgeon has access to the bones of the hip joint including the acetabulum, femoral head and femur. As with all approaches the muscles and soft tissue must be retracted in order to expose the bones below. Particularly with the minimal invasive (less extensile) anterior approach, the tensor fascia latae can often be under great tension creating difficulty in minimizing damage to the TFL tissue. Current tools and techniques do not have a dedicated retraction device for the TFL, and as such multiple surgical retractors that do not specifically fit the TFL are used. In addition during the anterior approach to hip exposure significant pressure is placed on the TFL while levering the proximal femur upwards to perform placement of the femoral component. The pressure can transect the TFL leading to patient injury, complications and lengthening the surgery. A dedicated TFL retractor and method of protecting the TFL band under tension during total hip replacement surgery would overcome the defects of current tools and procedures.

SUMMARY OF THE INVENTION

The present invention is a surgical apparatus, comprising a generally semi-circular elongate body having a distal end, a proximal end, and an elbow.

The generally semi-circular elongated body extends from the distal end to the proximal end and wherein the proximal end turns back toward back toward the distal end at elbow.

The elbow is sized to fit around and rest on the Anterior Hip Capsule and the angle of the elbow is adjustable by a surgeon.

The elongated body has a concave inner surface and a convex outer surface, and the radius of the concave surface is sized to allow the tensorfascia latae to fit within the walls of concave surface.

The semi-circular elongate body is made from a medically compatible polymer, selected from a group consisting of polyethylene (PE), Polytetrafluoroethylene (PTFE, Teflon), Polyetheylene (PET), Polyetherketone (PEK), Poly(methyl methacrylate) (PMMA), Polyvinyl chloride (PVC).

In an implementation example of the present invention, a method of use of the surgical apparatus comprising, a generally semi-circular elongate body further having a distal end, a proximal end, and an elbow. The generally semi-circular elongated band extends from the distal end to the proximal end and wherein the proximal end turns back toward back toward the distal end at elbow. The method includes inserting the surgical apparatus such that the elbow sits upon the Anterior Hip Capsule and tensor fascia latae tissue rests upon a longitudinal portion of the semi-circular elongated body. Retracting the tensor fascia latae tissue with a separate surgical instruments to expose thehip joint wherein the separate surgical instrument leverages against the surgical apparatus instead of directly against the tensor fascia latae tissue.

BRIEF DESCRIPTION OF THE DRAWINGS

The foregoing summary, as well as the following detailed description of the invention will be better understood when read in conjunction with the appended drawings. For the purpose of illustrating the invention, there are shown in the drawings embodiments which are presently preferred. It should be understood, however, that the invention can be embodied in different forms and thus should not be construed as being limited to the embodiments set forth herein.

FIG. 4A is a top view of the present invention depicted in FIG. 3;

FIG. 4B is a sectional view of the present invention depicted in FIG. 4A;

FIG. 4C is a left side view of the present invention depicted in FIG. 3;

FIG. 4D is a side view of the present invention depicted in FIG. 3; and

FIG. 4E is a bottom view of the present invention depicted in FIG. 3.

DETAILED DESCRIPTION

The present subject matter will now be described more fully hereinafter with reference to the accompanying figures, in which representative embodiment(s) are shown. The present subject matter can, however, be embodied in different forms and should not be construed as limited to the embodiments set forth herein. Rather, these embodiments are provided to describe and enable one of skill in the art. Unless otherwise defined, all technical and scientific terms used herein have the same meaning as commonly understood by one of ordinary skill in the art to which the subject matter pertains. All publications, patent applications, patents and other references mentioned herein are incorporated by reference in their entirety.

By some estimates damage or injury to the TFL during total hip replacement surgery, including those using the direct anterior approach, occurs in as much as 35% of procedures and represents a significant deterrent to surgeons using this method.

Figure 1:
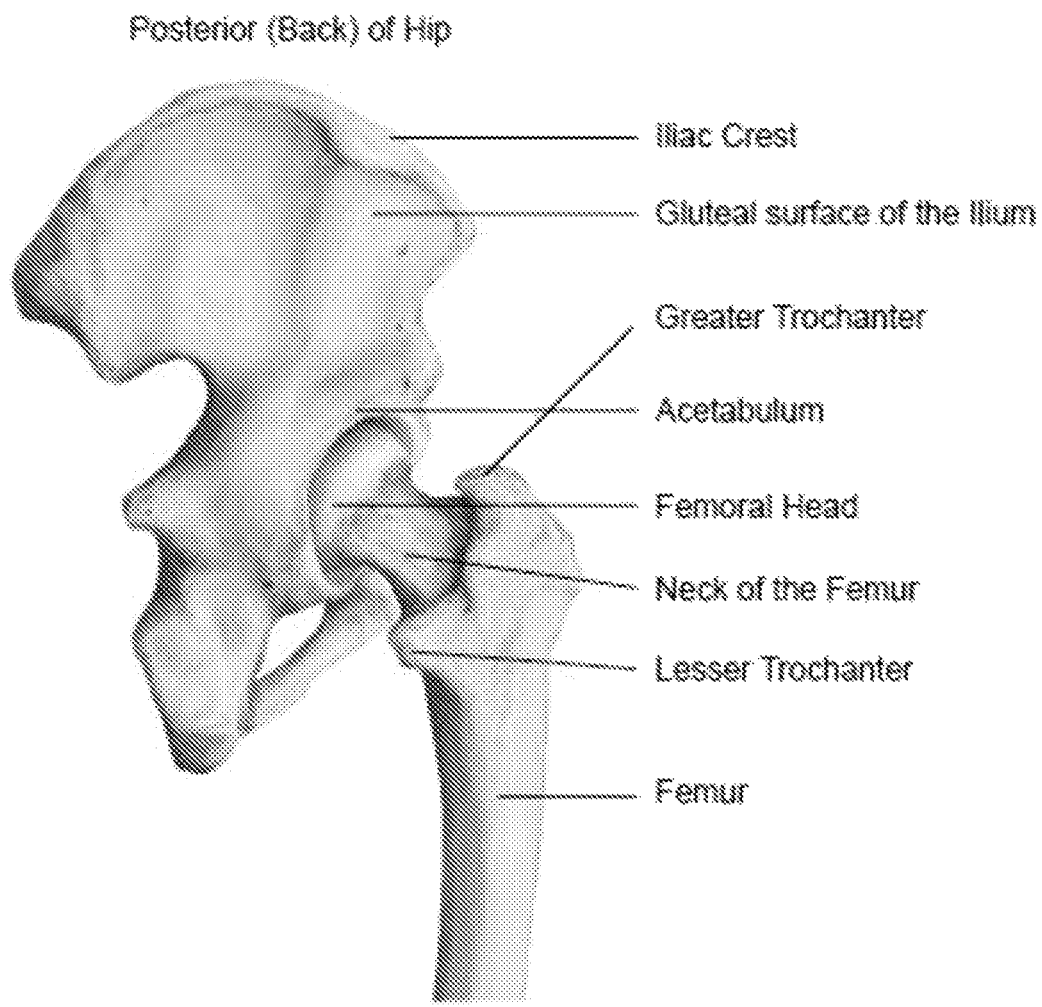
FIG. 1 illustrates the anatomy of the human hip.
Figure 2:
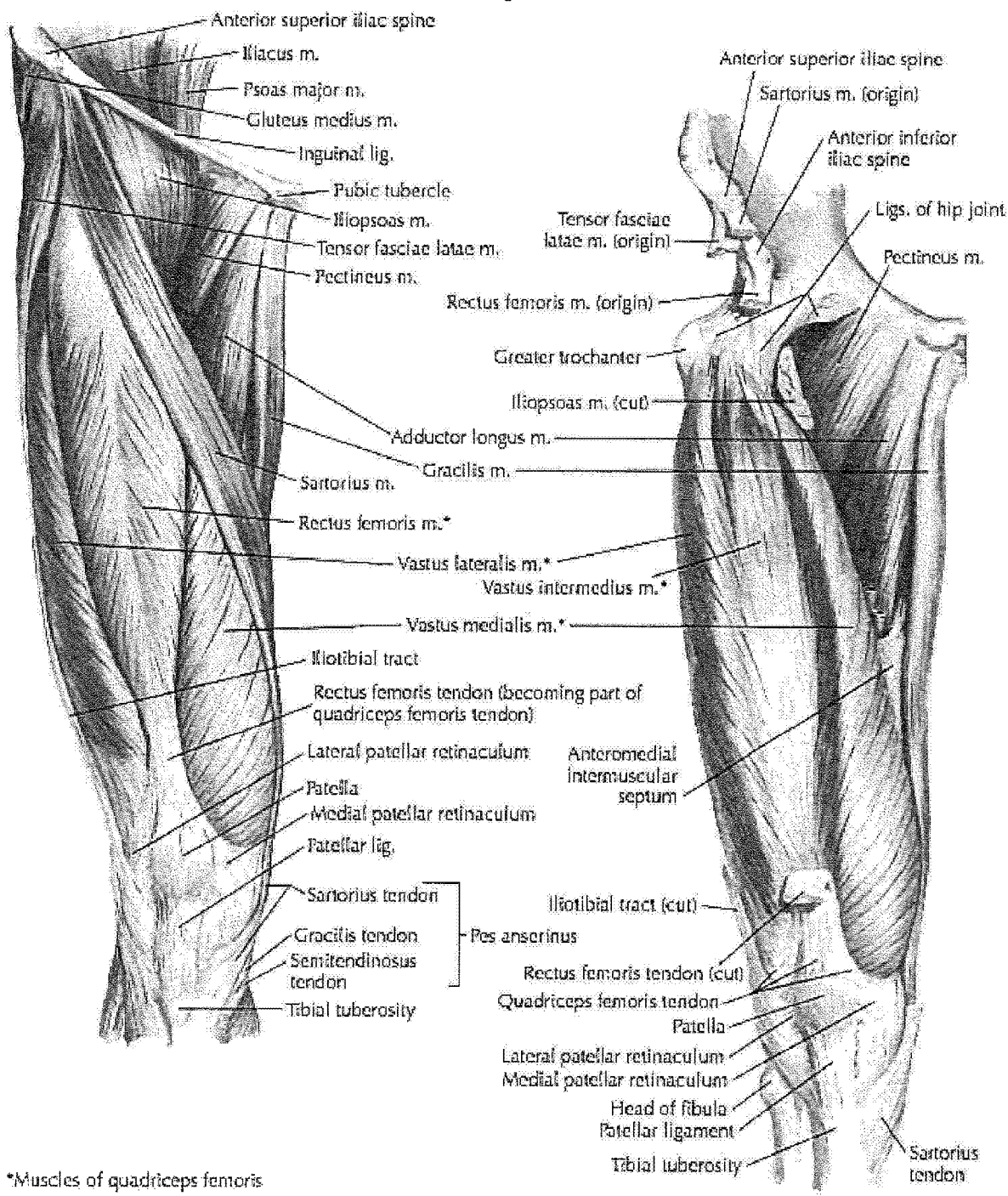
FIG. 2 further illustrates the anatomy of the human hip.
Figure 3:
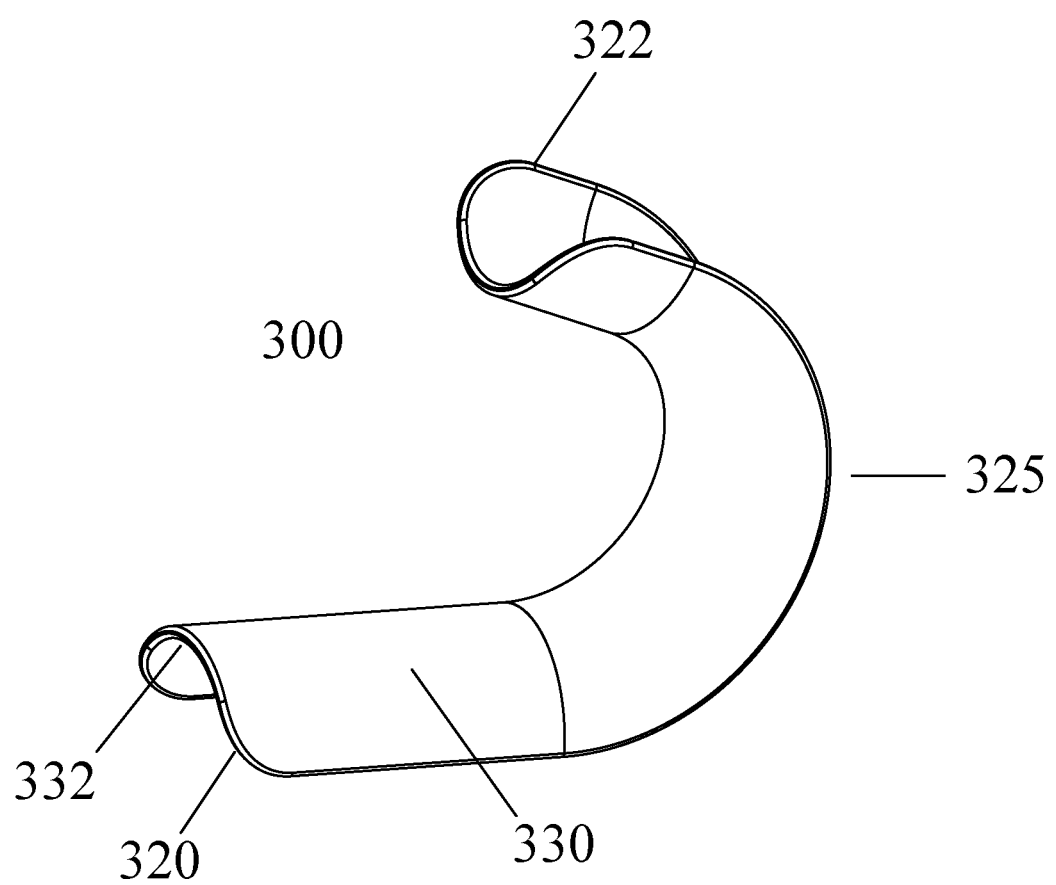
FIG. 3 is a perspective view of the an embodiment of the present invention.

Referring to FIG. 3, the TFL Protector 300 is a curvilinear insert and is provided for use, for example, during the anterior approach to obtain hip exposure. The TFL protector 300 is temporarily inserted during surgery between the sartorius and the TFL to distribute and dissipate force from elevation of the femur during exposure. In use, the TFL Protector 300 can protect against and reduce the incidents of iatrogenic injury to the TFL during the direct anterior approach.

The example embodiment illustrated in FIGS. 3 and 4A-E comprises the TFL Protector 300 is a longitudinal semi-circular channel having a distal end 320, a proximal end 322, elbow 325, a convex outer surface 330 and a concave inner surface 332. The TFL Protector 300 has a generally semi-circular or U-shaped elongated body extending from the distal end 320 to the proximal end 322, wherein the proximal end 322 turns back toward back toward the distal end 320 at elbow 325. The TFL Protector 300 has a generally longitudinal aspect extending from the distal end 320 to the elbow 325, which may in some embodiments establish a longitudinal axes xy. The semi-circular or U-shaped dimension of the convex surface 330 and concave surface 332 are generally centered on the longitudinal axis xy. The TFL Protector 300 turns away from the longitudinal axes in a manner generally perpendicular to the xy line such that the proximal end 322 is raised from the longitudinal axis xy thereby forming elbow 325.

The TFL Protector has an overall length ("L") that is measured from the distal end 320 to the outside of elbow 325. Various embodiments of the TFL Protector allow for different sizes, such that it is envisioned that there be multiple sizes (ex. Small, Medium, Large, Extra-Large) available, depending on the needs of the surgeon and the physical characteristics of the patient. The preferable sizes identified below are merely exemplary dimensions and should not be construed as limiting the available sizes of the TFL Protector. In some embodiments the length L of the device is between 2.5 and 4.5 inches, and preferably 3.5 inches. The TFL Protector has an overall height ("OH") of between 1.5 and 3.5 inches and preferably 3.0 inches. The OH is vertical height/distance between the distal end 320 and the proximal end 322. The internal height ("IH") of the device 300 is vertical height/distance between the inside surface of the distal end 320 and the proximal end 322 and is between 1 and 3 inches, and preferably 1.7 inches. The width ("W") of the device can be between 1 and 2 inches, and preferably 1.5 inches. In some embodiments the wall thickness ("T") of the device between the convex surface 330 and the concave inside surface 332 is between 0.030 and 0.125 inches and preferably 0.075 inches. In some embodiments the radius ("R") of the concave inside surface 332 surface is approximately 0.625 inches. The concave inside surface 332 is sized to allow the tensor fascia latae to rest within the walls of the concave inside surface such that other surgical tools used during the operation can rest against the surface of the TFL Protector without coming into contact with the tensor fascia latae. The angle α formed at elbow 325 can be between approximately 20 degrees to 160 degrees such that the elbow 325 circumvents the Anterior Hip Capsule.

The TFL Protector 300 can be made a variety of materials and techniques to achieve a semi-rigid construction of the present invention. The TFL Protector 300 may be made of a medically compatible polymer. Examples include polyethylene (PE), Polytetrafluoroethylene (PTFE, Teflon), Polyetheylene (PET), Polyetherketone (PEK), Poly(methyl methacrylate) (PMMA), Polyvinyl chloride (PVC) or any other biocompatible polymer. In other examples the TFL Protector 300 is made from stainless steel, aluminum, or other biocompatible metal. In still other examples the device is made of a biocompatible metal and coated with a biocompatible polymer. In still other examples the device is made using a solid construction. In still other examples the device is a woven construction. In still other examples the device is a layered construction, as in 3-D printing. In still other examples the device is laminate construction. The device may be cast, molded, extruded, woven, laminated, stamped, pressed or printed.

In the direct anterior approach to THA, the interval developed is between the Sartorius and the TFL tissue. Without a TFL Protector 300, during broaching, a femoral elevator levers on the TFL and can transect the TFL if too much force is used. An advantage of using the TFL Protector 300 with the direct anterior approach is that when performed correctly there is no muscle that is split or removed from the bone. In use, the TFL Protector 300 is placed between the Sartorius and the TFL such that elbow 325 rests on the Anterior Hip Capsule and is designed to protect the TFL during broaching when a femoral elevator is used and lever on the TFL. That is, at least a part of the TFL sits within the concave surface 332 along the longitudinal portion of the TFL Protector 300. The proximal end is inserted first into the patient. Femoral elevator, retractors and/or other surgical instruments used to expose the hip joint levers against the TFL Protector 300 and not directly against the TFL tissue. The TFL Protector 300 is held in place by the force of the femoral elevator. When the broaching and stem implantation are complete, the TFL Protector 300 is removed and may be discarded.

The TFL Protector 300 may be utilized for other approaches where muscles are in jeopardy of being damaged by the force of retractors.

In alternate embodiments the geometry of the device may be altered, for example the device may have a generally flat shape, slightly curved shape, or L-shape. The device may or may not include elbow 325. The device may be rigid or semi-rigid. The location of elbow 325 and angle α may be fixed, adjusted or set by the surgeon.

Various geometries and shapes are possible and within the scope of the invention, such that the TFL Protector 300 is placed against the tissue of the TFL thereby preventing direct contact between other surgical instruments and the TFL during retraction of the TFL. Use of the TFL Protector 300 allows for exposure of the bones of the hip joint without common complications.

It should be understood that various changes, substitutions, additions and alterations can be made by one skilled in the art without departing from the spirit and scope of the invention as defined by the appended claims. Moreover, the scope of the present application is not intended to be limited to the particular embodiment(s) of the device, process, machine, manufacture and composition of matter, means, methods and or steps described in the specification. As one of ordinary skill in the art will readily appreciate from the disclosure herein, processes, machines, manufacture, composition of matter, means, methods or steps, presently existing or later to be developed that perform substantially the same function or achieve substantially the same result as the corresponding embodiments described herein may be utilized according to the present invention.

The invention claimed is:

1. A method of use of a surgical apparatus comprising:
providing a surgical apparatus comprising,
a generally semi-circular channel elongate body further comprising:
   a distal end,
   a proximal end, and
   an elbow, wherein the elbow is sized to fit around and rest on an Anterior Hip Capsule; and
   wherein the surgical apparatus has a generally longitudinal aspect from the distal end to the elbow such that when the proximal end turns back toward the distal end the surgical apparatus has a J-shaped configuration;
inserting the surgical apparatus such that the elbow sits upon the Anterior Hip Capsule and tensor fascia latae tissue rests upon a longitudinal portion of the generally semi-circular channel elongate body,
wherein the channel is sized such that that tensor fascia latae tissue is adapted to rest within channel walls of the surgical apparatus;
retracting the tensor fascia latae tissue with a separate surgical instrument to expose the hip joint wherein the separate surgical instrument leverages against the surgical apparatus instead of directly against the tensor fascia latae tissue so as to distribute and dissipate forces acting on the tensor fascia latae tissue.

2. The method of use of claim 1, wherein an angle of the elbow is adjustable by a surgeon.

3. The method of use of claim 1, wherein the generally semi-circular channel elongate body has a concave inner surface and a convex outer surface.

4. The method of use of claim 1, wherein the generally semi-circular channel elongate body is made from a medically compatible polymer.

5. The method of use of claim 4, wherein the medically compatible polymer is selected from a group consisting of polyethylene (PE), Polytetrafluoroethylene (PTFE, Teflon), Polyetheylene (PET), Polyetherketone (PEK), Poly(methyl methacrylate) (PMMA), and Polyvinyl chloride (PVC).

\* \* \* \* \*